US012558527B2

(12) United States Patent
Fech et al.

(10) Patent No.: US 12,558,527 B2
(45) Date of Patent: Feb. 24, 2026

(54) INSTRUMENT FOR FLUID APPLICATION AND CLAMPING DEVICE

(71) Applicant: Erbe Elektromedizin GmbH, Tuebingen (DE)

(72) Inventors: Andreas Fech, Tuebingen (DE); Frank Straub, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 787 days.

(21) Appl. No.: 17/883,766

(22) Filed: Aug. 9, 2022

(65) Prior Publication Data

US 2023/0055098 A1 Feb. 23, 2023

(30) Foreign Application Priority Data

Aug. 10, 2021 (EP) ..................................... 21190538

(51) Int. Cl.
*A61M 39/28* (2006.01)
*A61M 5/30* (2006.01)

(52) U.S. Cl.
CPC ............ *A61M 39/288* (2013.01); *A61M 5/30* (2013.01); *A61M 39/285* (2013.01)

(58) Field of Classification Search
CPC ........ A61M 39/288; A61M 2205/3337; A61M 39/28; A61M 5/30; A61M 39/285; A61M 2205/273; F16K 7/068; F16K 7/06; F16K 7/02; F16K 7/04
See application file for complete search history.

(56) References Cited

U.S. PATENT DOCUMENTS

| | | | |
|---|---|---|---|
| 2,540,364 A | 2/1951 | Adams | |
| 4,453,696 A | 6/1984 | Witt | |
| 4,525,163 A * | 6/1985 | Slavik | A61M 5/1689 |
| | | | 128/DIG. 13 |
| 5,460,490 A * | 10/1995 | Carr | A61M 1/7415 |
| | | | 417/474 |
| 6,056,260 A | 5/2000 | Stewart | |
| 6,183,437 B1 * | 2/2001 | Walker | A61F 2/0022 |
| | | | 604/27 |

(Continued)

FOREIGN PATENT DOCUMENTS

| | | | |
|---|---|---|---|
| CA | 2690197 A1 * | 12/2008 | .............. A61M 1/74 |
| CN | 101641538 A | 2/2010 | |

(Continued)

OTHER PUBLICATIONS

National Intellectual Property Administration, PRC; Office Action in corresponding Chinese Patent Application No. 202210953669.7, dated Oct. 9, 2024; 13 pages.

(Continued)

*Primary Examiner* — Cris L. Rodriguez
(74) *Attorney, Agent, or Firm* — Fitch, Even, Tabin & Flannery LLP

(57) ABSTRACT

For producing a high pressure impulse, a hose bending valve is provided that comprises a loop (12) provided in a supply hose of an instrument (2) and a hose bending device (8) provided as multiple-use component. Such a valve is very simply constructed and allows the creation of steep pressure increase flanks with very high pressures up to 100 bar, as are needed for a needleless injection. The sterilization effort is minimal. Also, the material effort is minimal, if single-use components are used.

15 Claims, 4 Drawing Sheets

(56)     References Cited

U.S. PATENT DOCUMENTS

| | | | | |
|---|---|---|---|---|
| 6,228,048 | B1 * | 5/2001 | Robbins | A61M 3/0279 604/27 |
| 7,469,874 | B2 | 12/2008 | Akahori | |
| 7,798,996 | B1 * | 9/2010 | Haddad | A61M 5/16831 417/477.2 |
| 8,361,040 | B2 * | 1/2013 | Spohn | A61M 5/14546 604/174 |
| 9,095,656 | B2 | 8/2015 | Gonon | |
| 9,566,188 | B2 * | 2/2017 | Raney | A61M 1/74 |
| 9,604,014 | B2 * | 3/2017 | Haddad | A61M 5/365 |
| 10,569,022 | B2 | 2/2020 | Fech et al. | |
| 2003/0196693 | A1 * | 10/2003 | Schwindt | A61M 1/77 251/5 |
| 2010/0168535 | A1 * | 7/2010 | Robinson | A61B 5/14532 600/309 |
| 2010/0234809 | A1 | 9/2010 | Kenley et al. | |
| 2011/0196304 | A1 * | 8/2011 | Kramer | A61M 5/1483 604/151 |
| 2011/0313394 | A1 * | 12/2011 | Bobo, Sr. | A61M 5/142 604/151 |
| 2013/0188040 | A1 * | 7/2013 | Kamen | G16H 40/63 348/135 |
| 2015/0045725 | A1 * | 2/2015 | Smith | A61B 1/31 604/26 |
| 2019/0160227 | A1 * | 5/2019 | Li | A61M 39/28 |
| 2020/0261711 | A1 * | 8/2020 | Spataro | A61M 39/10 |
| 2020/0306450 | A1 | 10/2020 | Enderle et al. | |

FOREIGN PATENT DOCUMENTS

| | | | | | |
|---|---|---|---|---|---|
| DE | 1837385 | U | 9/1961 | | |
| DE | 69815825 | T2 | 5/2004 | | |
| DE | 602004009494 | T2 | 7/2008 | | |
| DE | 102010017216 | A1 * | 12/2011 | | A61M 37/0076 |
| EP | 2130562 | A2 | 12/2009 | | |
| EP | 2133610 | A1 | 12/2009 | | |
| EP | 3040101 | B1 | 7/2016 | | |
| EP | 3714926 | A1 | 9/2020 | | |
| GB | 1012565 | | 12/1965 | | |
| JP | 2010-538761 | A | 12/2010 | | |
| JP | 2012-519544 | A | 8/2012 | | |
| WO | 9841254 | A1 | 9/1998 | | |
| WO | WO-2024115437 | A1 * | 6/2024 | | A61M 1/153 |
| WO | WO-2025101650 | A1 * | 5/2025 | | A61B 1/307 |

OTHER PUBLICATIONS

National Intellectual Property Administration, PRC; Search Report in corresponding Chinese Patent Application No. 202210953669.7, dated Oct. 8, 2024; 6 pages.

European Search Report in EP 21190538 dated Feb. 9, 2022 (7 pages).

Japan Patent Office; Notice of Reasons for Refusal in corresponding Japanese Patent Application No. 2022-125694, dated Oct. 20, 2025; 11 pages.

* cited by examiner

INSTRUMENT FOR FLUID APPLICATION AND CLAMPING DEVICE

RELATED APPLICATION(S)

This application claims the benefit of European Patent Application No. 21190538.5, filed Aug. 10, 2021, the contents of which are incorporated herein by reference as if fully rewritten herein.

TECHNICAL FIELD

The invention refers to an instrument for fluid application as well as a hose bending device for blocking and unblocking of a fluid hose.

BACKGROUND

An application system is known from EP 3 714 926 A1 by means of which medical fluids can be introduced in biological tissue in a needleless manner. For this purpose a first fluid channel is provided in the instrument via which a sharp jet of a fluid can be emitted that serves for opening of an injection channel in the tissue. Via a further fluid channel the medical fluid, e.g. a liquid containing living cells, is supplied with low pressure that can now enter into the tissue via the opened injection channel.

For emitting a sharp fluid jet to efficiently open the injection channel in the biological tissue it is important that the increase of the fluid pressure at the distal end of the instrument at the beginning of the emission of a sharp injection jet is as steep as possible. In doing so, it shall be guaranteed that the created jet has its full penetration ability from the beginning and that as little as possible liquid is deposited in layers preceding the target tissue and thus does not reach the target tissue.

EP 3 040 101 B1 discloses a device for creation of pressure increase flanks that are as steep as possible. Valves are provided for blocking and unblocking of fluid channels that are under pressure. These valves need to be entirely configured in a sterilizable manner or they have to be configured as single-use components.

Independent therefrom, they have to be in any case suitable to suddenly unblock or also block a remarkable fluid pressure of up to 100 bar.

For opening and unblocking fluid channels, so-called pinch valves are known. An example is disclosed in U.S. Pat. No. 9,095,656 B2. The pinch valve described there is realized by a flexible line section that is arranged inside of a pressure container. This pressure container also serves as energy source for the creation of a fluid jet. Due to the arrangement of a flexible hose inside the pressure container, the pressure in the line interior is always approximately equal to the pressure outside of the supply line. Therefore, the valve drive only needs to overcome the spring-back force of the wall of the flexible line element. Thus, only low blocking forces result. The unblocking of the fluid channel is carried out by means of the spring-back force of the wall and is only little supported by the fluid pressure due to the small pressure difference between the pressure inside the fluid channel and the pressure outside of the hose. This can lower the steepness of the pressure increase during opening of the valve.

So-called bend valves are also known. For this U.S. Pat. No. 2,540,364 discloses a hose provided with multiple finger loops. The finger loops can be pulled over finger and thumb of a hand of a user, who can then bend or unblock the hose by a simple hand movement.

Further mechanized devices for bending and unblocking of a hose are known from GB 1 012 565, DE 698 15 825 T2, EP 2 133 610 A1 or EP 2 130 562 A2.

DE 60 2004 009 494 T2 discloses a device with multiple bending sites arranged one after another at a hose that form valves, wherein the bending sites are defined by means of two eccentric discs. These bending sites or valves are alternatingly opened and closed by means of cam discs in order to release and discharge small fluid portions with low pressure from a high pressure fluid reservoir. In addition, a simple magnetic operated bending valve is disclosed in U.S. Pat. No. 6,056,260.

It is one object of the invention to provide a concept for an instrument and an assigned valve by means of which fluid that is under high pressure can be discharged in impulses with steep pressure increase flank and for which only low efforts are required.

SUMMARY

This object is solved on one hand with an instrument and on the other hand with the hose bending device as disclosed herein.

According to the invention, the instrument comprises a first fluid hose that can be connected to a first fluid source in order to supply the instrument with fluid that is under high pressure. The first fluid hose of the instrument itself is used as valve. For this purpose it is inserted in a hose bending device according to claim 9 that comprises an actuation device in order to selectively bend or unblock a loop formed by the fluid hose. For simplifying the insertion of a loop of the fluid hose in the hose bending device, according to claim 1 a holder can be arranged on the fluid hose, in order to hold the fluid hose in a loop. The loop can then be handled like a connector and can be inserted in a respective channel of the hose bending device. This concept separates the components on the instrument side that are easily sterilizable or also always providable for replacement with low efforts and are thus providable as single-use parts from the components on the apparatus side that are not or only in a difficult manner sterilizable and are providable for replacement respectively, only with high efforts. Each bending valve is therefore entirely realized by an apparatus side component, namely the hose bending device, as well as the first fluid hose of the instrument.

The fluid supply to the instrument via the first fluid hose can be under high pressure and can be supplied in impulses with steep pressure increase flank respectively in order to create an injection channel in the biological tissue. The instrument can comprise a second fluid hose, the proximal end of which can be connected to a second fluid source. The latter can be under a different, particularly lower, pressure in order to discharge medical fluid after opening of the injection channel, which is inserted in the opened injection channel and thus into the biological tissue by means of the instrument or fluid applicator.

While the first fluid hose is held in a loop by the holder in order to be inserted in the hose bending device, the second fluid hose is preferably configured or guided without bends and loops. It is, however, also possible to also guide the second fluid hose through a hose bending device in order to use its bending site as valve.

The loop defined by the holder comprises preferably two legs that are held substantially parallel to each other by means of the holder. The length L of the loop, particularly the length of its legs, is thereby preferably longer than the distance of the two legs from each other, which defines its width B. The length L and the width B are thereby adapted to each other, such that the loop is open in its rest condition. It bends and therefore closes with only one bend, if the width B is decreased by means of the hose bending device.

Preferably the holder is fixedly, that means immovably, arranged on the first fluid hose. Thereby the holder determines the size of the loop and thus also the position of the loop relative to the actuation device of the hose bending device as soon as the holder together with the loop is inserted in the channel of the hose bending device like a plug. Thus, a correct function is guaranteed.

However, instead of the holder, also other means for limiting the insertion depth of the loop into the channel can be provided. For example, a stop means, e.g. a wall, can be provided behind the actuation device in insertion direction against which the loop abuts, if it is inserted in the channel. In this case the wall forms a positioning means for definition of the loop position relative to the actuation device. In such loop bending devices sections of a fluid hose can be inserted that are formed into a loop, wherein the fluid hose does not comprise a holder. In connection with the hose bending device according to claim 8, also instruments can be used that are not configured in a manner according to claim 1.

In hose bending devices that do not have such a positioning means mentioned above, the holder provided on the first fluid hose of the instrument can take over the function of this positioning means. Then the holder gets into abutment against a wall located in front of the actuation device in insertion direction that concurrently, by forming a plug stop, limits the insertion depth of the loop.

Further details of advantageous embodiments of the invention are subject of the figure of the drawing, the associated description as well as dependent claims. The drawings show:

DETAILED DESCRIPTION

Figure 1:
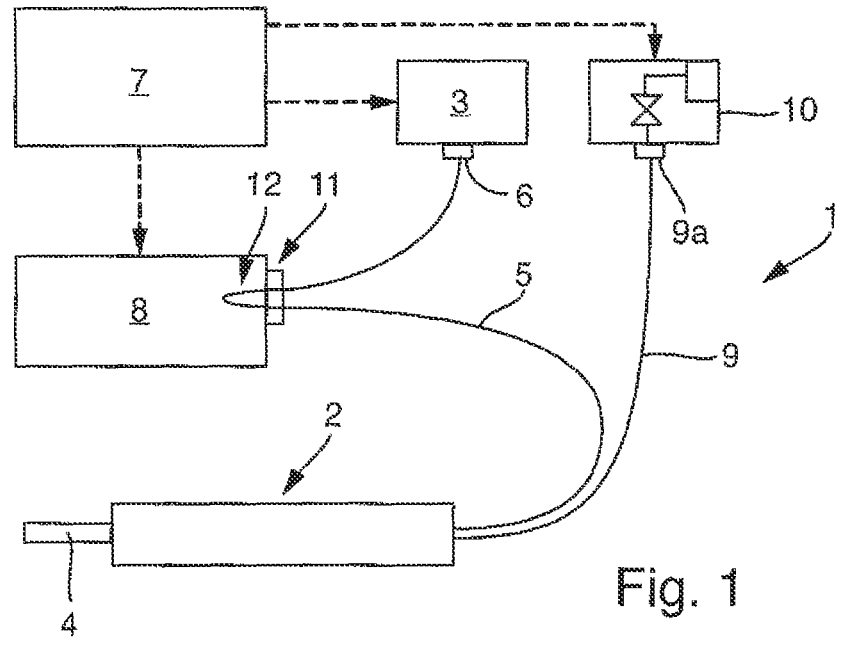
FIG. 1 a treatment device comprising an instrument and a hose bending device according to the invention, FIG. 2 the hose bending device and a part of a fluid hose of the instrument according to FIG. 1 in a schematic illustration in part, FIG. 3 the fluid hose and the hose bending device according to FIG. 2 in a perspective separated illustration, FIG. 4 the arrangement according to FIG. 2 in perspective illustration, FIG. 5 a slightly modified embodiment of a hose bending device comprising a fluid hose in open condition, FIG. 6 the hose bending device according to FIG. 5 and the fluid hose of the instrument in closed condition, FIG. 7 a modified embodiment of the hose bending device with closed fluid hose, FIG. 8 the hose bending device according to FIG. 7 with open fluid hose, FIG. 9 a modified embodiment of an instrument and of a supplying apparatus with hose bending device in perspective illustration, FIG. 10 an instrument with hose bending device in schematic illustration and FIG. 11 a modified embodiment of the hose bending device.

In FIG. 1 a device 1 for treatment of a patient by means of injection of medical liquid is illustrated. An instrument 2 that can be, for example, guided manually and further devices and components for supplying the instrument 2 with one or more liquids are part of the device 1. A first fluid source 3 is part of these components that contains, for example, fluid under high pressure, e.g. sodium chloride solution. The pressure is sufficiently high in order to supply a fluid applicator provided on the instrument 2 with fluid being under injection pressure. The injection pressure is so high that a fluid jet discharged from the fluid applicator 4 penetrates biological tissue and opens an injection channel there. Apart from physiological saline solution, the fluid source 3 can also contain and provide other biologically compatible fluids.

The instrument 2 is or can be connected with the fluid source 3 via a first fluid hose 5. For this purpose the fluid hose 5 can be provided with a plug 6 on its proximal end. Its distal end is, however, preferably undetachably, as necessary however also releasably connected with instrument 2.

The fluid source 3 can be configured to continuously provide pressurized fluid via plug 6 to the instrument 2. However, fluid source 3 can also comprise valves or other control elements in order to specifically unblock or block the pressurized fluid. For control of the fluid source 3 a control device 7 can be provided.

The fluid applicator 4 requires fluid under high pressure provided by the fluid source 3, preferably in impulses with steep pressure increase flanks. For providing and creating such pressure impulses, a hose bending device is provided that can be controlled by the control device 7. The hose bending device 8 together with a section of the fluid hose 5 form a high pressure valve for blocking and unblocking of fluid inside fluid hose 5.

Via a second fluid hose 9, instrument 2 can be connected with a second fluid source 10 that provides a second fluid, particularly a fluid serving as medicine, a cell suspension or the like. The second fluid source can provide the fluid with a lower pressure continuously or in impulses. For control of the fluid discharge, the second fluid source 10 can comprise a valve that can be controlled by means of the control device 7. The fluid hose 9 can be connected to the fluid source 10 by means of a plug 9a.

Figure 2:
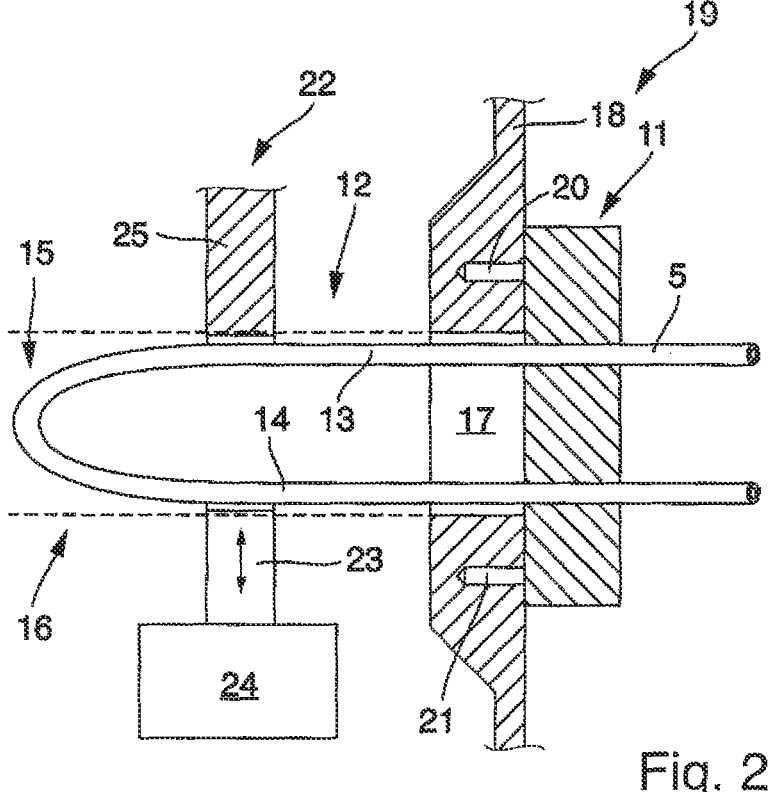

The hose bending device 8 and the fluid hose 5 together form a high pressure valve that is illustrated in FIG. 2 in a basic illustration. The fluid hose 5 consists of a suitable common plastic, such as PU, PFA, FEP, KPFA, KEEP, PVC, silicone, PA, TPE-S or any other suitable plastic. Fiber-reinforced or armored plastic hoses can be used.

The hose 5 is held in a holder 11 that is arranged between the proximal and the distal end of fluid hose 5, preferably in proximity of plug 6, as apparent from FIG. 1. The holder 11 is fixedly attached on fluid hose 5 in order to hold a section of fluid hose 5 in a loop 12. This loop comprises two legs 13, 14 that are substantially parallel to each other and that transition into each other at a loop head 15. The fluid hose comprises a stiffness such that it bends at a site with the largest curvature, namely at the loop head 15, if the two legs 13, 14 are moved toward one another, thereby blocking its lumen, without collapsing the lumen at another site due to pinching.

Holder 11 together with loop 12 forms a plug. The loop 12 of the so formed plug can be inserted into an insertion area 16 that is illustrated in a manner bordered by dashed lines in FIG. 2. The entrance of insertion area 16 is formed by a slot-like opening 17 that is formed on a front wall 18 of the hose bending device 8. The wall 18 is therefore concurrently a positioning means 19 for the plug or the holder 11. Pins 20, 21 can be provided on holder 11 that fit into respective openings inside wall 18 in order to fixate and position holder 11 on the wall 18. Instead of the pins 20, 21 also other connection and positioning means can be present, e.g. permanent magnets or other mechanical or non-mechanical latching means.

The insertion area 16 is the space that the loop 12 takes in its released condition. It extends through an actuation device 22 that is configured to move the legs 13, 14 against their own spring tension toward one another. Thereby the actuation device is preferably arranged closer to the loop head 15 than to the holder 11. The actuation device 22 can comprise a movable element 23 that is configured to urge leg 14 in direction toward leg 13. Accordingly, the element 23 can be in connection with a drive device 24. The element 23 can be arranged linearly movably or also pivotably.

Opposite the element 23 a further element 25 can be arranged that can be configured as rigid abutment. Alternatively, the element 25 can also be movably arranged toward element 23 and connected with a respective drive device (not illustrated).

FIG. 3 again shows the configuration illustrated in FIG. 2 in a perspective manner. As apparent, the insertion area 16 is again realized by opening 17 at a respective opening between element 25 serving as abutment and the movable element 23 covered by drive device 24 in FIG. 3.

Figures 3, 4, 5, 6:
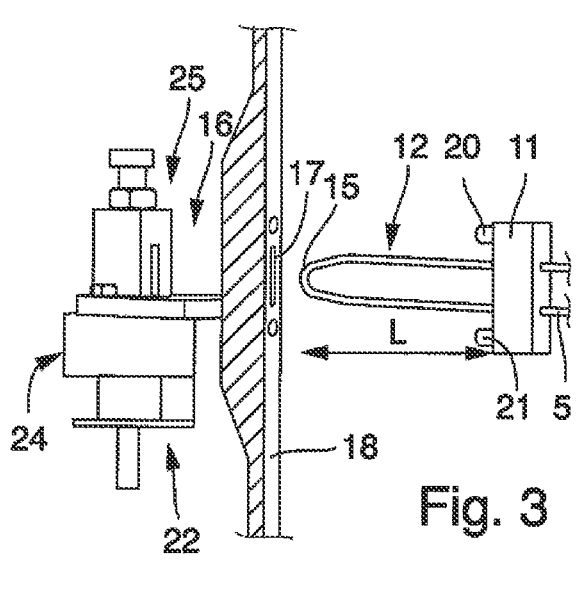

FIG. 4 illustrates loop 12 being inserted into the hose bending device 8. The holder 11 abuts against wall 18. The loop 12 extends through the actuation device 22. The loop head 15 is located behind the actuation device 22 with view from the wall 18.

In the embodiment described so far holder 11 defines the insertion depth of loop 12 into the hose bending device 8. The wall 18 is thus (together with the holder 11) the positioning means for the loop 12.

It is, however, also possible to define the insertion depth of loop 12 by means of a stop 26 for the loop head 15, as apparent from FIGS. 5 and 6. The stop 26 then in turn forms the positioning means 19. In such an embodiment of the hose bending device 8 holder 11 can be omitted or holder 11 can be arranged with longer distance to the front wall 18. Also holders 11 can be used that are arranged on fluid hose 5 not immovably, but displaceably (e.g. slideably).

The drive device 24 can be configured as magnet drive. For example, a coil 27 can be provided in the center of which an armature 28 is arranged that is immovably connected with the movable element 23. A spring 29 can serve to keep the armature 28 and the element 23 therewith in rest position outside the insertion area 16.

The actuation device 22 and the loop 12 together form a valve. The fluid side part of the valve is formed by the loop 12 that is part of the instrument 2. The part of the valve that is not in contact with the fluid is realized by the hose bending device 8 that can be configured as separate device or that can be part of a device that comprises the control device 7 as well as the fluid sources 3 and 10.

For injection of fluid in biological tissue the device 1 described so far operates as follows:

After connection of instrument 2 to the fluid sources 3 and 10 the plug formed by holder 11 and loop 12 is inserted into the hose bending device 8, as illustrated in FIG. 2, 4 or 5. Thus, the device 1 is basically ready for operation.

After switching control device 7 on, the control device 7 determines the correct connection of instrument 2 to fluid sources 3 and 10 as well as the insertion of loop 12 into the hose bending device 8. Now the control device 7 closes the valve formed by loop 12 and hose bending device 8, as illustrated in FIG. 6, in that coil 27 is supplied with current.

In doing so, armature 28 is pulled into coil 27 and thereby the element 23 is urged against element 25 serving as abutment. The two legs 13, 14 are moved toward one another, such that the fluid hose 5 bends at the loop head 15. The fluid channel is blocked in this condition and no high pressure fluid can pass to the instrument 2.

The abutment 24 is preferably arranged so that the leg 13 remains substantially undeformed. The movement of element 23 is preferably defined so that it leaves the cross-section of leg 14 substantially undeformed in the retracted condition and in case it is moved maximum in direction toward the abutment 24, it keeps a distance thereto. The distance is preferably at least two times as large as the diameter of the fluid hose. In this manner pinching of the fluid hose 5 is avoided. In other words, the fluid cross-section remains substantially circular in the area of the actuation device, its lumen is open (not pinched) here.

Prior to closing this valve, fluid hose 5 can be purged with fluid in order to eliminate air that is present inside fluid hose 5 and instrument 2 as well as applicator 4. For this purpose the control device discharges fluid from the fluid source 3 preferably with reduced pressure for a short period prior to closing the valve formed by loop 12.

If now a medical treatment fluid shall be applied to a patient, fluid 3 that is under high pressure is first used by the instrument and the fluid applicator 4 for opening an injection channel. For this purpose the control device 7 switches the coil 27 for a short period in a power-off condition. The armature 28 is thereby no longer attracted. The spring 29 urges armature 28 out of coil 27, whereby the position according to FIG. 5 is reached. The bend at the loop head 15 is eliminated and suddenly fluid with high pressure reaches the fluid applicator 4. The high fluid pressure supports the hose in its opening movement. The fluid applicator 4 emits a sharp fluid jet that is able to open an injection channel into the biological tissue.

Although an already highly steep pressure increase can be achieved at the fluid applicator 4 by means of this concept, the pressure increase can be yet configured steeper. If the armature 28 is, for example, configured as permanent magnetic armature moving the movable element 23 out of the insertion area 16 can yet be accelerated in that the coil 27 is not currentless for opening the valve, but is powered with inverse polarity. Moreover, a spring that is effective between the legs 13, 14 can accelerate the pivot movement of the legs 13, 14 away from one another.

Figures 7, 8, 9:
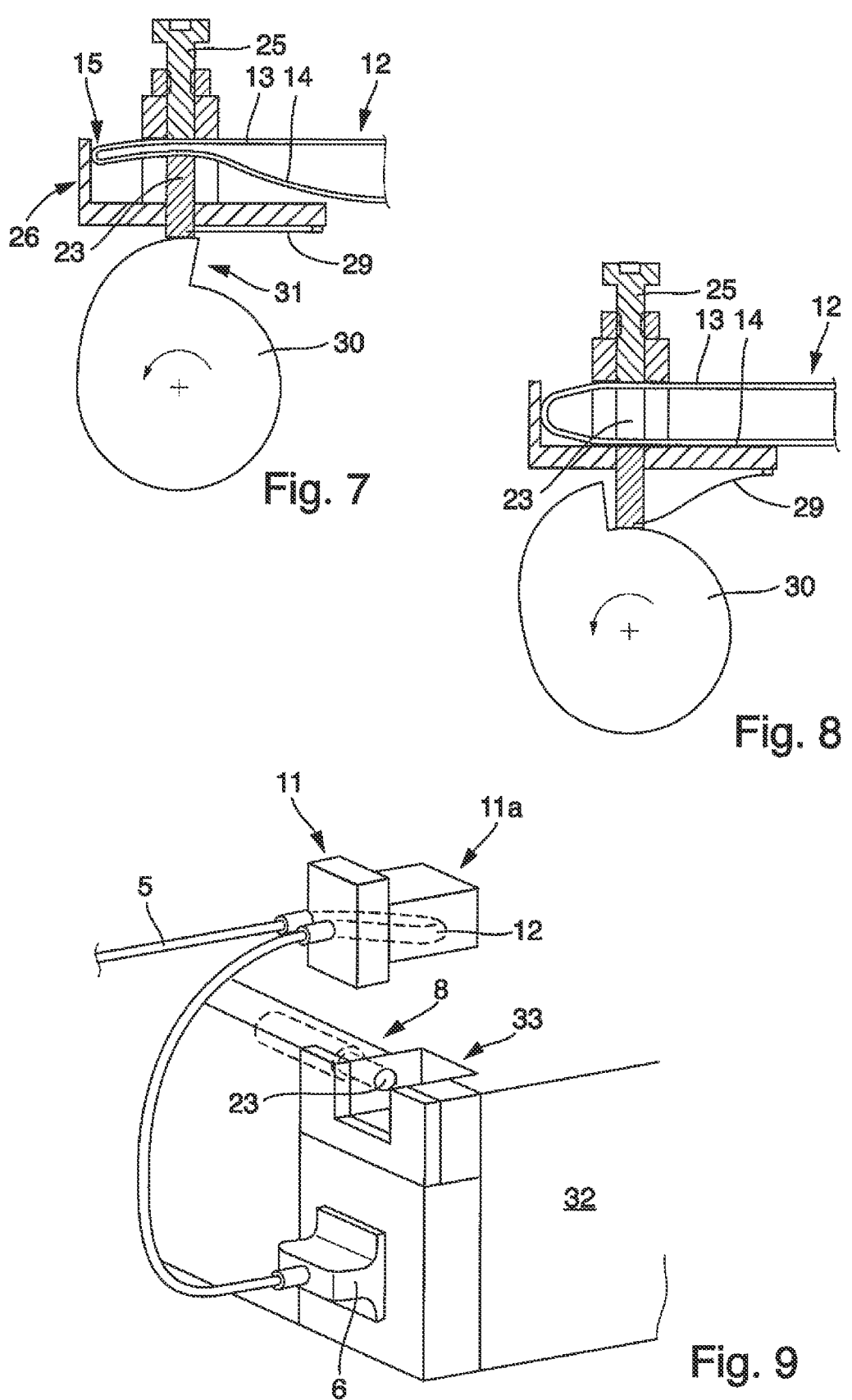

For this purpose FIG. 7 and FIG. 8 illustrate another efficient possibility. The movable element 23 is here actuated by means of a cam disc 30 that can comprise one or multiple cams. For example, the circumference of the cam disc 30 can follow a spiral and can comprise a recess 31 at the end thereof. The cam disc 30 can be in abutment with its spiral-shaped circumference against movable element 23 that operates as cam follower. A suitable spring means, e.g. spring 29 configured as leaf spring, keeps the movable element 23 in abutment against cam disc 30.

For example for closing the valve, a suitable motor, e.g. a stepper motor, can be provided that rotates the cam disc 30 until the element 23 reaches the highest point on the circumference of the cam disc 30. If the valve shall now be opened, the stepper motor rotates the cam disc 30, as illustrated in FIG. 8, slightly further such that the movable element 23 reaches and passes recess 31. Under the effect of the back spring force of legs 13 and 14 of loop 12 and under the effect of spring 29, the element 23 jumps practically without delay in its rest position such that opening of the valve is carried out with most possible speed.

Figure 11:
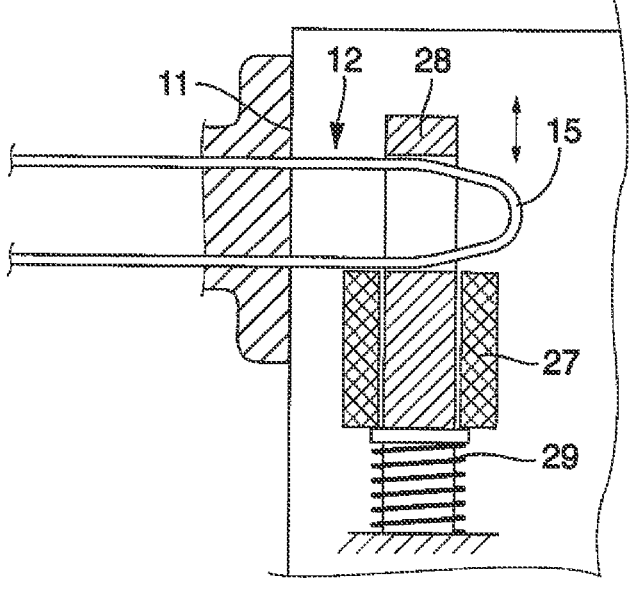

FIG. 11 illustrates another variation of the actuation device 22. There the armature 28 comprises a slot, the width of which is slightly larger than the diameter of fluid hose 5 and therefore allows the lateral guide of loop 12 on one hand, but also the movement of hose in opening and closing direction on the other hand. In doing so, armature 28 defines a portion of the insertion area 16.

The spring 29 urges the armature 28 in the illustrated unblocked position. During powering of coil 27, armature 28 is pulled downward in FIG. 11 such that the loop 12 bends at the loop head 15. Apart therefrom, a description of the preceding embodiments applies accordingly.

FIG. 9 illustrates an apparatus 32 that includes the fluid sources 3 and 10 as well as the hose bending device. The holder 11 holds the loop 12 in a sub-housing 11a that also comprises an abutment surface for one of the two legs 13 or 14. Opposite the sub-housing 11a comprises an opening through which a plunger can enter into the sub-housing 11a in order to bend the loop 12. The plunger can in turn be realized by a movable element 23 that is actuated by means of a suitable actuator, e.g. an electromagnet or a cam disc. In the sub-housing 11a a spring means can be arranged that is arranged between the legs 13, 14 and acts upon leg 14. The spring means can provide a force that encounters the bending of the hose head.

For holding sub-housing 11a in the hose bending device, the latter comprises a receptacle 33 that functionally corresponds to the insertion area 16. The receptacle can be open toward the top, as illustrated in FIG. 9, or also configured as insertion channel.

Figure 10:
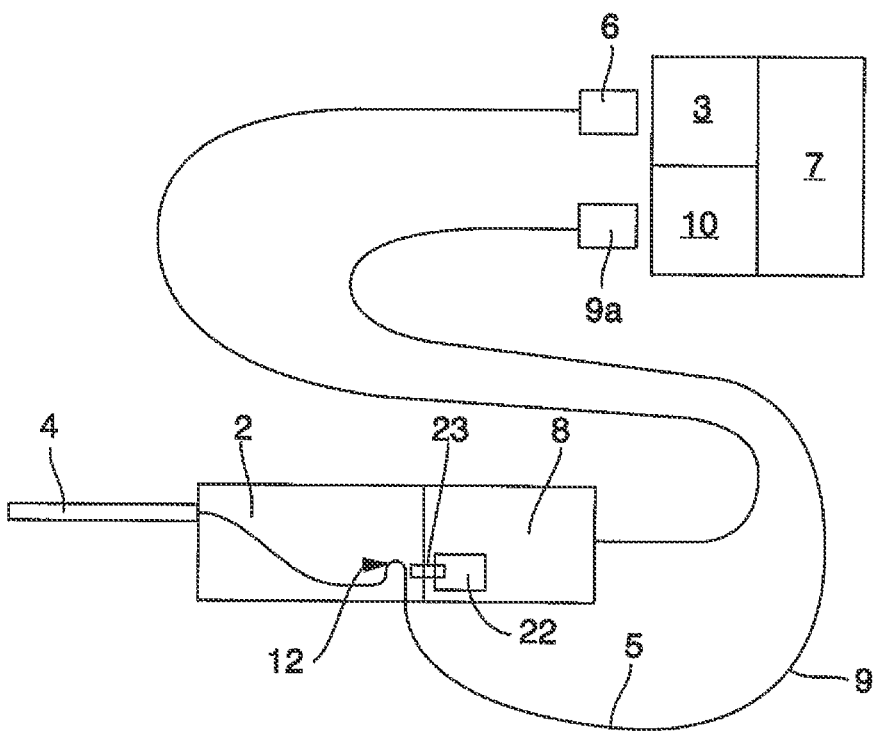

FIG. 10 illustrates another important modification of the inventive concept. There the hose bending device 8 is configured as multiple-use component of a single-use instrument 2. The hose bending device 8 comprises the actuation device 22 and is releasably connected with the handle of instrument 2. In the connected condition the movable element 23 of actuation device 22 can extend into the single-use component and can act on loop 12 there in order to bend or unblock it. The control of the actuation device 22 is carried out by means of a respective control connection to the control device 7, e.g. via a not illustrated line.

According to the concept according to the invention, for producing a high pressure impulse a hose bending valve is provided that comprises a loop 12 provided in a supply hose (fluid hose 5) of an instrument 2 and a hose bending device 8 provided as multiple-use component. Such a valve is very simply constructed and allows the creation of steep pressure increase flanks with very high pressures up to 100 bar, as they are needed for a needleless injection. The sterilization effort is minimum. Also the material effort is minimum, if single-use components are used.

| List of Reference Signs: | |
| --- | --- |
| 1 | device |
| 2 | instrument |
| 3 | first fluid source |
| 4 | fluid applicator |
| 5 | first fluid hose |
| 6 | plug |
| 7 | control device |
| 8 | hose bending device |
| 9 | second fluid hose |
| 10 | second fluid source |
| 11 | holder |
| 11a | sub-housing |
| 12 | loop |
| 13, 14 | leg of loop 12 |

-continued

| List of Reference Signs: | |
| --- | --- |
| 15 | loop head |
| 16 | insertion area |
| 17 | opening |
| 18 | front wall |
| 19 | positioning means |
| 20, 21 | pins |
| 22 | actuation device |
| 23 | moveable element |
| 24 | drive device |
| 25 | element |
| 26 | stop |
| 27 | solenoid |
| 28 | armature |
| 29 | spring |
| 30 | cam disc |
| 31 | recess |
| 32 | apparatus |
| 33 | receptacle |

The invention claimed is:

1. An instrument (2) comprising:
a fluid applicator (4);
a first fluid hose (5) that extends from a proximal end thereof to the fluid applicator (4), wherein the proximal end is configured to be connected to a first fluid source (3); and
a holder (11) that is arranged on the first fluid hose (5) that holds the first fluid hose (5) in a loop (12);
wherein the holder (11) comprises at least one connection means (20, 21) for connection with a hose bending device (8).

2. The instrument according to claim 1, wherein the fluid applicator (4) comprises a second fluid hose (9) that is configured to be connected at its proximal end (9a) to a second fluid source (10).

3. The instrument according to claim 2, wherein the second fluid hose (9) extends from its proximal end (9a) to the fluid applicator (4) without a bend and without a loop.

4. The instrument according to claim 1, wherein the loop (12) has a length (L) that is longer than its width (B).

5. The instrument according to claim 1, wherein the loop (12) comprises two legs (13, 14) held in the holder (11) that are parallel to one another.

6. The instrument according to claim 1, wherein the loop (12) is immovably held in the holder (11).

7. The instrument according to claim 1, wherein the instrument (2) is configured as single-use instrument.

8. A hose bending device (8) comprising:
a holder (11) configured to be fixedly positioned on first and second legs (13, 14) of a fluid hose (5) such that the fluid hose forms a loop (12) projecting from the holder (11) with the first and second legs (13, 14) extending along an insertion direction and being connected at a free head (15) of the loop (12) such that the holder (11) and the loop (12) form a plug;
an insertion area (16) configured to receive the loop (12) of the fluid hose (5) inserted in the insertion direction; and
an actuation device (22) arranged at or about the insertion area (16) configured to deform or release the loop (12) in a controlled manner.

9. The hose bending device according to claim 8, wherein the insertion area (16) comprises a slot cross-section of the actuation device (22).

10. The hose bending device according to claim 8, further comprising a positioning means (19) for defining a position of the loop (12) relative to the actuation device (22).

11. The hose bending device according to claim 10, wherein the positioning means (19) is a stop (26) arranged behind the actuation device (22) in the insertion direction.

12. The hose bending device according to claim 10, wherein the positioning means (19) is a plug stop (18) arranged in front of the actuation device (22) in the insertion direction.

13. The hose bending device according to claim 8, wherein the hose bending device (8) is configured as a sterilizable device.

14. A system comprising an instrument (2) according to claim 1 and a hose bending device (8) comprising:

an insertion area (16) configured to receive the loop (12) of the fluid hose (5) inserted in an insertion direction; and an actuation device (22) arranged at or about the insertion area (16) configured to deform or release the loop (12) in a controlled manner.

15. The instrument according to claim 1, wherein the at least one connection means (20, 21) comprises at least one of a pin and a magnet.

* * * * *